(12) United States Patent
Kovalan

(10) Patent No.: US 9,106,609 B2
(45) Date of Patent: Aug. 11, 2015

(54) METHOD AND SYSTEM FOR FAST ACCESS TO ADVANCED VISUALIZATION OF MEDICAL SCANS USING A DEDICATED WEB PORTAL

(71) Applicant: Kovey Kovalan, Stamford, CT (US)

(72) Inventor: Kovey Kovalan, Stamford, CT (US)

(*) Notice: Subject to any disclaimer, the term of this patent is extended or adjusted under 35 U.S.C. 154(b) by 0 days.

(21) Appl. No.: 14/187,996

(22) Filed: Feb. 24, 2014

(65) Prior Publication Data

US 2014/0195922 A1    Jul. 10, 2014

Related U.S. Application Data

(63) Continuation of application No. 13/322,359, filed as application No. PCT/US2010/036355 on May 27, 2010, now Pat. No. 8,701,167.

(60) Provisional application No. 61/181,695, filed on May 28, 2009.

(51) Int. Cl.
*G06F 7/04*        (2006.01)
*G06F 17/30*      (2006.01)
(Continued)

(52) U.S. Cl.
CPC .............. *H04L 67/02* (2013.01); *G06F 3/0484* (2013.01); *G06F 19/321* (2013.01); *G06T 15/08* (2013.01);
(Continued)

(58) Field of Classification Search
CPC ....................... G06F 21/606; G06F 2221/2141
USPC .......................................................... 726/4
See application file for complete search history.

(56) References Cited

U.S. PATENT DOCUMENTS 6,621,918 B1      9/2003  Hu
2004/0041846 A1*  3/2004  Hurley et al. ............ 345/848
(Continued)

FOREIGN PATENT DOCUMENTS

KR    10-1999-0057669    7/1999
KR    2002-00041577      6/2002
(Continued)

OTHER PUBLICATIONS

Renato Pajarola; Large scale Terrain Visualization using the Restricted Quadtree Triangulation; date: 1998; Institute of Theoretical Computer Science; p. 1-27.*
(Continued)

*Primary Examiner* — Monjour Rahim
(74) *Attorney, Agent, or Firm* — DeLio, Peterson & Curcio, LLC; Peter W. Peterson

(57) ABSTRACT

A system for viewing at a client device a series of three-dimensional virtual views over the Internet of a volume visualization dataset contained on centralized databases employs a transmitter for securely sending volume visualization dataset from a remote location to the centralized database, more than one central data storage medium containing the volume visualization dataset, and a plurality of servers in communication with the centralized databases to create virtual views based on client requests. A resource manager load balances the servers, a security device controls communications between the client device and server and the resource manager and central storage medium. Physically secured sites house the components. A web application accepts at the remote location user requests for a virtual view of the volume visualization dataset, transmits the request to the servers, receives the resulting virtual view from the servers, and displays the resulting virtual view to the remote user.

31 Claims, 5 Drawing Sheets

(51) Int. Cl.

| | | |
|---|---|---|
| *H04N 7/16* | (2011.01) | |
| *H04L 29/08* | (2006.01) | |
| *G06F 19/00* | (2011.01) | |
| *G06T 15/08* | (2011.01) | |
| *G06F 3/0484* | (2013.01) | |
| *H04L 29/06* | (2006.01) | |

(52) U.S. Cl.
CPC ............ *H04L 63/04* (2013.01); *H04L 63/0428* (2013.01); *H04L 63/083* (2013.01); *G06T 2210/08* (2013.01); *G06T 2210/41* (2013.01)

(56) References Cited

U.S. PATENT DOCUMENTS

| | | | |
|---|---|---|---|
| 2007/0130165 A1 | 6/2007 | Sjoblom | |
| 2008/0043015 A1 | 2/2008 | Valdeserri | |
| 2008/0195843 A1 | 8/2008 | Muniandy | |
| 2009/0016641 A1 | 1/2009 | Paladini | |
| 2009/0018996 A1* | 1/2009 | Hunt et al. ........................ | 707/2 |
| 2009/0116757 A1 | 5/2009 | Neogi et al. | |
| 2010/0094758 A1 | 4/2010 | Chamberlain et al. | |
| 2010/0134484 A1 | 6/2010 | Chen et al. | |
| 2011/0302138 A1 | 12/2011 | Cesario | |

FOREIGN PATENT DOCUMENTS

| | | |
|---|---|---|
| KR | 20030057669 | 3/2005 |
| WO | WO03-088030 | 10/2003 |
| WO | WO2005-036457 | 4/2005 |

OTHER PUBLICATIONS

Fabrizio Lamberti et al. "A Streaming-Based Solution for Remote Visualization of 3D Graphics on Mobile Devices", IEEE Transactions on Visualization and Computer Graphics, IEEE Service Center Los Alamitos, CA, US; vol. 12, No. 2; Mar. 1, 2007, pp. 247-260 XP011157909.

Engel K. et al "Combining Local and Remote Visualization Techniques for Interactive Volume Rendering in Medical Applications", Proceedings Visualization 2000, Salt Lake City, UT, Oct. 13, 2000, pp. 449-452 XP031385622.

* cited by examiner

METHOD AND SYSTEM FOR FAST ACCESS TO ADVANCED VISUALIZATION OF MEDICAL SCANS USING A DEDICATED WEB PORTAL

This application claims priority from U.S. patent application Ser. No. 13/322,359 filed Nov. 23, 2011 which is a National Stage Application of PCT/US2010/036355, filed May 27, 2010 which claims priority from U.S. provisional application No. 61/181,695, filed on May 28, 2009.

BACKGROUND OF THE INVENTION

1. Field of the Invention

This invention relates to a method and system for viewing at a client computer a series of three-dimensional virtual views, transmitted over the Internet, of a volume visualization dataset contained on one or more centralized databases.

2. Description of Related Art

The demand for easy access to medical scans is increasing and the expectation for a simpler and faster way to interpret these large scans is growing. Technology exists to present richer three-dimensional (3D) views from existing two-dimensional (2D) scans that may lead to better diagnosis and prognosis as well as improved patient care. However, the current solutions are impractical for 3D to be ubiquitous.

Computed Axial Tomography (CT) scans or magnetic resonance imaging (MRI) scans of a patient's body results in large 3D volume datasets that is time consuming when transported over the Internet. The scans are typically spaced two-dimensional planar cross-sections of the patient's body or a portion thereof, such as an organ. The scans of these or other objects may be stored as a volume visualization dataset in an otherwise conventional data storage medium accessible by a computer or other specialized processor. Assuming the scans are parallel images arranged in the sequence in which they are found in the scanned object, 3D virtual views of the volume visualization dataset are made by selecting a plane to be cut through the volume of the object at a particular location and angle. The selected plane may be parallel to the scans, or at any angle to the scans. The location may be anywhere within the scanned volume of the object. The 3D virtual image is a two-dimensional representation of the 3D object showing the desired perspective of view and may include images showing depth of or through the object in a direction normal to and behind the selected plane of view.

Generating dynamic 3D views requires processing of raw 2D scans in to 3D and to isolate feature of interest from the raw scan. Therefore, for 3D to be available, either the user's computer or a dedicated server needs to be powerful enough to support this processing power and the 2D scans need to be directly available to the user's computer via a high speed communication link. Facilities such as Hospitals and Imaging Centers need to provide the software, hardware, and networking infrastructure and support the IT administration to allow their physicians access to 3D. This becomes expensive and adds an administrative burden that only a select few provide such a "luxurious" functionality to their physicians. The present invention overcomes this limitation by teaching a method and system of a common and centralized infrastructure, for receiving, storing, processing and viewing large medical scans via a low-bandwidth web portal where economic of scale can be applied generously.

Internet access via web portal particularly low bandwidth and high latency situation of rural area can hinder the user interactivity of information presented in 3D. Latency, i.e., delay in the time it takes for a packet of data to travel from one designated point to another in response to a request, is particularly problematic for users having low bandwidth Internet communication. Unless otherwise noted, the term "low bandwidth" refers to communication speed of no more than about 1.5 Mbps, and the term "high latency" refers to response time of more than about 125 ms. The user may request arbitrarily and dynamically generated views. This requirement normally mandates that raw scan data needs to be present on the user's computer for manipulation. For large 3D, four-dimensional (4D), or higher dimensional scans, the retrieving or raw scan for processing is impractical or impossible over low bandwidth network. (Scans in 4D can come in the form of time varying 3D scans, or as a result of combining two datasets, such as PET and CT scanners dataset combined in one. Also, when PET-CT are combined and have a time component, this can be termed a 5D scan, which involves very large datasets.) The publication by Klaus Engel on Remote 3D Visualization Using Image-Streaming Techniques teaches how volume visualization can be obtained via a client and server interaction over the web without having to retrieve raw scan on to user machines. However, such technique requires sufficient bandwidth and low latency network to present information at interactive frame rates. This presents a problem for rural areas to gain access to medical scans in advanced visualization format interactively.

Furthermore, medical service providers are required to keep medical records for six years or more and have to do so with utmost security and privacy. This becomes expensive and adds a management burden to facilities as there can be IT, physical space and cost administration limitations. The end effect is that a facility's operation remains an ad hoc process.

SUMMARY OF THE INVENTION

Bearing in mind the problems and deficiencies of the prior art, it is therefore an object of the present invention to provide one or more of the following: 1) a method and system that overcomes low bandwidth and high latency limitations that are inherent properties of the standard Internet and permits bandwidth usage to be optimized, particularly for interactive web application for visualizing large medical scans and other volume visualization datasets on any Internet connection; 2) a method and system that overcomes the problems of maintaining medical records for long periods of time under security and privacy by providing a common and centralized infrastructure for receiving, storing, processing and viewing large medical scans via a web portal where economic of scale can be applied generously.

Still other objects and advantages of the invention will in part be obvious and will in part be apparent from the specification.

One or more of the above and other objects, which will be apparent to those skilled in the art, are achieved in the present invention which is directed to a system for viewing at a client device a series of three-dimensional virtual views over the Internet of a volume visualization dataset contained on at least one centralized database comprising at least one transmitter for accepting volume visualization dataset from remote location and transmitting it securely to the centralized database, at least one central data storage medium containing the volume visualization dataset, and a plurality of servers in communication with the at least one centralized database and capable of processing the volume visualization dataset to create virtual views based on client request. The system also comprises a resource manager device for load balancing the plurality of servers, a security device controlling the plurality of communications between a client device, and the server;

and between the resource manager and central storage medium, and at least one physically secured site for housing the centralized database, plurality of servers, at least a resource manager, and at least a security device. The system further comprises a web application adapted to satisfy a user's request by accepting at a remote location at least one user request for a virtual view of the volume visualization dataset, transmitting the request to at least one of the servers, receiving the resulting virtual view from the at least one server, and displaying the resulting virtual view to the user at the remote location.

The system secured site may be a SAS70 Type II Compliant or equivalent audited or tested data center. Multiple secured sites located on disparate physical location are connected via an intranet.

The web application may select a secured site by using a domain name address on a web browser and/or a secured site IP address of a resource manager by Domain Name System. The web application may be a medical device for diagnostic imaging viewing purpose. The web application may be authenticated using an authorized user credentials prior to transmitting the request to at least one of the servers.

The authenticated web application may list the volume visualization datasets that are viewable by the authorized user, and may initiate a virtual viewing by selecting a volume visualization dataset. The request for a virtual view of the volume visualization dataset may employ an XML document or web server on Hypertext Transfer Protocol Secure (HTTPS).

The web application may communicate with the resource manager device, and may be allocated with at least one server by the resource manager device. The web application is adapted to commence interaction with the server to satisfy user requests, and may be an Active-X component, a Java applet or JavaScript, Flash or Silverlight or other web browser scriptable language.

The system may further include an encrypted communication connection over which the request and the resulting virtual view are transmitted. The encrypted communication connection may employ SSL/TLS and may further include secure communication ports that communicate only with SSL/TLS turned on.

In another aspect, the present invention is directed to a method for viewing at a client device a series of three-dimensional virtual views over Internet of a volume visualization dataset contained on at least one centralized database. The method comprises providing at least one central data storage medium containing the volume visualization dataset, providing at least one server in communication with the at least one centralized database and capable of processing the volume visualization dataset to create virtual views based on client request, and providing a client device linked to the at least one server and central storage medium over the Internet, the client device having local data storage medium for storing frames of views of the volume visualization dataset. The method then includes requesting at the client device at least one three-dimensional virtual view of at least a portion of the volume visualization dataset, determining if any frame of the requested at least one view of the volume visualization dataset is stored on the local data storage medium, and sending from the client device to the server a request for any frame of the requested at least one view not stored on the local data storage medium. The method further includes, at the server, creating the requested frame of the requested at least one view from the volume visualization dataset in the central storage medium, transmitting the created frame of the requested at least one view from the server to the client device, and displaying the requested at least one three-dimensional virtual view of the volume visualization dataset at the client device by displaying either the frame transmitted from the server or any frame of the requested series of views stored on the local data storage medium.

The method of claim 17 including storing on the client device local data storage medium one or more frames transmitted from the server of the requested series of views that were not previously stored on the local data storage medium The volume visualization dataset may comprise a plurality of cross-sectional images taken at spaced intervals through an object. The client device may request a series of three-dimensional virtual view of at least a portion of the volume visualization dataset, with the series of views comprising a plurality of separate view frames. The requested series of three-dimensional virtual views of the volume visualization dataset may be displayed at the client device by sequentially displaying frames transmitted from the server along with any frames of the requested series of views stored on the local data storage medium. During the displaying of the requested series of three-dimensional virtual views of the volume visualization dataset at the client device, frames stored on the local data storage medium may be displayed along with frames transmitted from the server.

The method may include providing a plurality of central data storage media, with each data storage medium containing all or a portion of the volume visualization dataset, and may include selecting the data storage medium from which the requested frames of the requested series of views from the volume visualization dataset are created and transmitted.

The determination of storage of any frame of the requested at least one view of the volume visualization dataset on the local data storage medium may be by creating a unique identifiable key of a request by the client device of a three-dimensional virtual view of the volume visualization dataset, storing on the local data storage medium the unique identifiable key of a prior request by the client device of a three-dimensional virtual view, comparing the unique identifiable key of a current request by the client device of a three-dimensional virtual view with a stored unique identifiable key of a prior request by the client device of a three-dimensional virtual view, and determining if values of the current and prior unique identifiable keys are equivalent. If the values are equivalent, the method may include displaying from the local data storage medium a stored frame of the prior request of the three-dimensional virtual view. If the values are not equivalent, the method may include displaying a frame transmitted from the server of the current request by the client device of a three-dimensional virtual view. The method may further include associating the unique identifiable key of a prior request by the client device of a three-dimensional virtual view with a stored frame of the prior request of the three-dimensional virtual view. If the values are equivalent, the method may include determining location of the stored frame of the prior request of the three-dimensional virtual view on the local data storage medium, and using such location to display the stored frame.

In a further aspect, the present invention is directed to a method for viewing at a client device a series of three-dimensional virtual views of a volume visualization dataset contained on at least one centralized database. The method comprises providing at least one central data storage medium containing the volume visualization dataset, providing at least one server in communication with the at least one centralized database and capable of processing the volume visualization dataset to create virtual views based on client request, and providing a client device linked to the server and central storage medium over the Internet. The method then includes sending from the client device to the server a request for a plurality of three-dimensional virtual views of at least a portion of the volume visualization dataset. The plurality of views comprises a plurality of separate view frames, and the request includes a request for a lower image quality parameter for the frames and a request for a higher image quality parameter for the frames. The method also includes, at the server, creating the requested frames from the volume visualization dataset at the lower image quality parameter, and transmitting the lower image quality parameter frames to the client device, and displaying at least a portion of the requested lower image quality parameter frames at the client device. The method further includes, at the server, creating the requested higher image quality parameter frames from the volume visualization dataset, and transmitting the higher image quality parameter frames to the client device, and displaying the requested higher image quality parameter frames at the client device.

After transmitting the lower image quality parameter frames to the client device, the server may transmit the higher image quality parameter frames to the client device while the client device is displaying the lower image quality parameter frames. The client device may display the higher image quality parameter frames prior to or after completing display of the lower image quality parameter frames. The frames may be transmitted from the server to the client device as a compressed video stream, or as one or more single frames.

In yet another aspect, the present invention is directed to a method for viewing at a client device a series of three-dimensional virtual views of a volume visualization dataset contained on at least one centralized database. The method comprises providing at least one central data storage medium containing the volume visualization dataset, providing a server in communication with the at least one centralized database and capable of processing the volume visualization dataset to create virtual views based on client request, and providing a client device linked to the server and central storage medium over the Internet. The method then includes requesting at the client device a series of three-dimensional virtual views of at least a portion of the volume visualization dataset, with the series of views comprising a plurality of separate view frames. The method also includes separating at the client device the requested series of three-dimensional virtual views into different groups of frames, and sending from the client device to the server a request for a first group of frames, while delaying sending to the server a request for a second group of frames. The method further includes, at the server, creating the requested first group of frames from the volume visualization dataset, and transmitting the first group of frames to the client device, and displaying the requested first group of frames at the client device while simultaneously sending from the client device to the server a request for a second group of frames. The method also includes, at the server, creating the requested second group of frames from the volume visualization dataset, and transmitting the second group of frames to the client device while the client device is displaying the first group of frames, and displaying the requested second group of frames at the client device immediately following the first group of frames, to maintain proper sequential display of the requested series of three-dimensional virtual views.

There may be provided a plurality of servers in communication with the at least one centralized database and capable of processing the volume visualization dataset to create virtual views based on client request, and a security device controlling the plurality of communications between a client device, and the server and central storage medium.

The method may further include sending from the client device to the server a request for a subsequent group of frames while a previous group of frames is being displayed, creating at the server the requested second group of frames from the volume visualization dataset, transmitting the second group of frames to the client device while the client device is displaying the previous group of frames; and displaying the requested subsequent group of frames at the client device immediately following the previous group of frames to maintain proper sequential display.

The client device and server may be connected by a network having a latency time, and the requested groups of frames may be delayed in sending from the client device to the server in accordance with the latency time. The groups of frames are transmitted from the server to the client device as a compressed video stream, or as one or more individual frames. The requested frames may be stored at the client device local data storage medium.

The request for a first group of frames may also include a request for a lower image quality parameter for the frames. After transmitting the first group of frames to the client device at the requested lower image quality parameter, the server may transmit frames to the client device at a higher image quality parameter.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

In describing the preferred embodiment of the present invention, reference will be made herein to FIGS. 1-5 of the drawings in which like numerals refer to like features of the invention.

Figure 1:
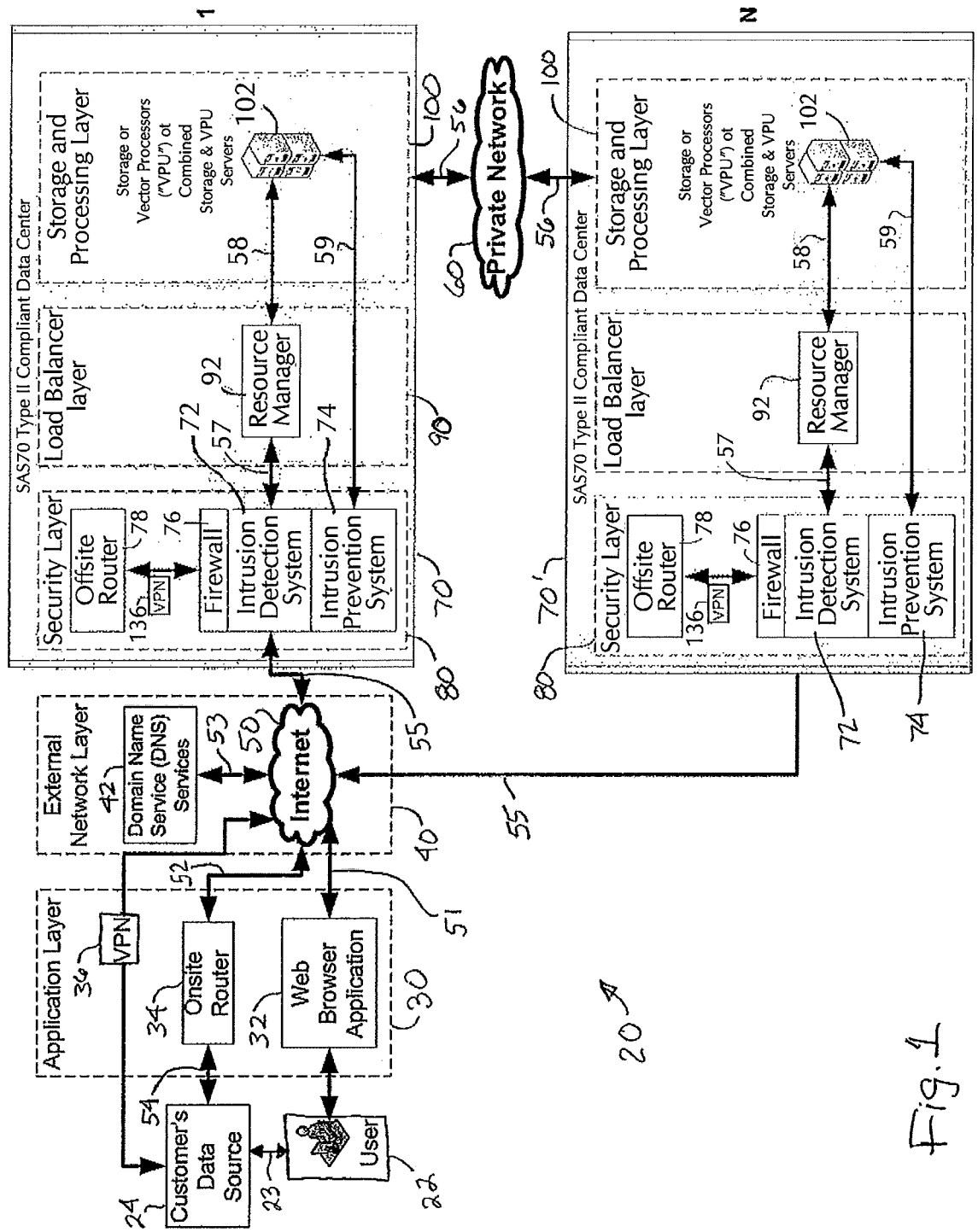
FIG. 1 is a schematic showing the major components and their interaction in operation of the present invention system and method for viewing at a client computer a series of three-dimensional virtual views over the Internet of a volume visualization dataset contained on at least one centralized database.

The present invention in one embodiment provides a method and system for fast access to advanced visualization of medical scans using a dedicated web portal, in particular, advanced visualization of volumetric data, for example, medical scans. As shown in FIG. 1, one embodiment of the method and system 20 of the present invention consists of a number of functional components or layers, i.e., Application Layer 30, External Network Layer 40, Security Layer 80, Load Balancer Layer 90, and Storage and Processing Layer 100. Communication and transmission connections between the individual system components or layer, as well as with the server and users, may be made by wireless, wireline, optical fiber cable, radio frequency (RF) or the like, and may also be made via an internal network (LAN), wide area network (WAN) and/or over the Internet or other connection means. The individual system components may be incorporated as hardware or software modules within a computer. Communication and transmission connections that permit a higher data transmission rate are preferred, although the present invention is particularly useful where low bandwidth and high latency situations exist between the user and the volumetric data.

The customer or user uses an otherwise conventional web browser application 32 on a computer or other electronic device 22 at a remote location capable of communicating across an intranet or the Internet, which device also may have connection 23 with a local computer-readable storage medium 24 that may be used as the customer's data source. Storage medium 24 may be employed to receive all or portions of volume visualization dataset(s) such as CT or MRI scans made elsewhere, and function as a transmitter of such dataset(s) to a centralized database, as will be discussed further below. Storage medium 24 may also be employed to receive and store downloads from the centralized database of all or portions of volume visualization dataset(s) or views created there from. One or more computer readable medium(s) may be utilized, alone or in combination. A suitable computer readable storage medium may be, for example, but not limited to, an electronic, magnetic, optical, electromagnetic, infrared, or semiconductor system, apparatus, or device, or any suitable combination of the foregoing. Other examples of suitable computer readable storage medium would include, without limitation, the following: an electrical connection having one or more wires, a portable computer diskette, a hard disk, a random access memory (RAM), a read-only memory (ROM), an erasable programmable read-only memory (EPROM or flash memory), an optical fiber, a portable compact disc read-only memory (e.g., CD-ROM), an optical storage device (e.g., DVD ROM), a magnetic storage device (e.g., diskette), or any suitable combination of the foregoing. A suitable computer readable storage medium may be any tangible medium that can contain, or store a program for use by or in connection with an instruction execution system, apparatus, or device.

At the Application Layer 30, there may be one or many web browser application(s) 30 and one or many onsite router(s) 34. The Application Layer is connected to External Network Layer 40 that employs the Internet 50 or any other network that connects the local network in the application layer to the rest of the layers using an encrypted channel of communication (such as SSL/TLS). Secure communication ports may be used that communicate only with SSL/TLS turned on, for example, a 443/8443/9443/custom port. This connection may be a high or low bandwidth connection 51 between the web browser and the Internet, and may include connection 54 between the customer data source 24 and onsite router 34, and connection 52 between the onsite router and the Internet. A virtual private network (VPN) 36 may also be used between the customer data source and the Internet. The connection may be facilitated by one or many domain name service (DNS) lookup services 42 and may be used to serve as a load balancer as well for directing traffic for when one or many serving physical sites or servers within it are down.

The External Network Layer connects via connections 55 to one or many serving sites 70, 70' that comprise of Security Layer 80, Load Balancer Layer 90 and Storage and Processing Layer 100. The Security Layer may consist of one or many firewall(s) 76, intrusion detection system(s) 72, and intrusion prevention system(s) 74. Load Balancer Layer 90 may contain at least two resource manager servers 92 with master and slave configuration. Load Balancer Layer 90 manages the allocation and expansion of servers to handle the scalability of storage capacity and processing power dynamically as Storage and Processing Layer 100 communicates with the user 22 through the Security Layer. At the Storage and Processing Layer there may lay a cluster of servers 102 that have storage capabilities and high performing vector processors. Servers 102 communicate with Security Layer 80 via connections 57 and 58 through resource manager 92, or directly via connection 59. The Security, Load Balancer and Storage and Processing Layers may be located physically at a serving site 70. For redundancy, one or many duplicate Security, Load Balancer and Storage and Processing Layers are located physically at one or more additional serving sites 70'. Serving sites 70, 70' may be connected with each other via External Network Layer 40. Additionally or alternatively, Storage and Processing Layers 100 at disparate locations 70, 70' may be connected via a private network 60 via connections 56 so that information exchange between them can be fast.

Storage and Processing Layer servers 102 may consist of server clusters having one or more computer-readable volume data storage medium (as described above), volume processing server, and web or application server for application interaction. The servers 102 are in communication with the computer-readable volume data storage mediums at the serving sites and are capable of processing volume datasets in the data storage mediums and communicating with the viewing applications of the visualization of the processed information. The Storage and Processing servers may receive data transmitted from a user's storage medium 24 by manual upload through the web browser application 30. Alternatively, the Storage and Processing servers may receive data from storage medium 24 transmitted through an onsite router 34 installed at the data source or an offsite router 78 installed at the Security Layer 80, connected via a single or bidirectional VPN 36, 136, respectively. The router 34, 78 may be configured to access existing storage infrastructure at the source location, and may be configured to move the source data from the source location to the Storage and Processing servers. The data movement may either be done through manual methods by authorized personnel accessing the router, or through automatic rules that may be setup prior to use. Rule criterion may be but not limited to moving data using a particular date interval, or based on the volume type, or a volume data belonging to a particular user or institution, etc. A router negotiates with the load balancer layer to identify which storage device server is available to accept a particular data. The criterion for selecting which storage device is available is determined but not limited to by the size of the volume data and the capability of the server to accept the volume data. Once data is available on the volume data storage device servers, information about the data is entered to a database and may be presented to user for visualization by the web portal.

Advanced visualization of volume datasets begin with identification of the volume datasets or subset of the datasets to visualize; specified as a user interaction parameter. The identification may include (a) the full volume datasets, (b) one or many planar views through volume datasets with each planar view having variable thickness, (c) curvilinear sampling of the volume datasets, (d) a region of interest sampling of the volume datasets, or (d) segmented volume datasets to simplify and/or change the representation of the volume datasets into something that is more meaningful and easier to analyze. The identified set of volume dataset may be then visualized by (a) applying a color, opacity, gradient, and/or multidimensional based transfer function to the intensity value of each individual voxels, and (b) using ray casting or texture based rendering techniques. Based on user interaction parameters, object transformation, projection transformation, clipping and screen transformation are applied to produce a rendered frame, a list of user interaction sequence generates one or many frames.

User 22 interactions to access advanced visualization of volumetric data via a web portal may begin with a web application 30 for accepting a user or a program login and listing the volume data description associated with the login, then launching a viewing application that is executable through a web browser. The viewing application takes a user or program input and communicates with one or many Storage and Processing servers 102, and displays the processed information as an advanced visualization of the volume data. For example, a customer or operator such as a physician, a patient, or a program logs in to volume visualization web portal using a web browser and identifies as an authorized user 22. A list of volume data such as a list of patient CT scans that is associated with the authorized user is presented to web application 30. The user may select one or more static or dynamic virtual images from the volume visualization dataset and request to view the images on the web application.

Static 3D virtual images may be made by selecting a plane to be cut through the volume of the object at a particular angle, at the desired location within the scanned volume of the object. Dynamic 3D virtual images may be made by moving the selected view plane through the volume of the scanned object, for example, by rotating it about a line, or by moving its center along a path, or a combination of both. This results in a series of 3D virtual views. The series of views comprise plurality of separate view frames created sequentially at different times during the movement of the view plane. Each frame contains the image information from the portions of the original scans that it intersects, and may further contain image information interpolated between the original scans. When the view frames are played back and displayed on a screen in the same sequence, the user is able to view the requested series of 3D virtual views in the manner of viewing a video. A request for a 3D virtual image is referred to herein as an interaction, and the movement of the view plane is referred to herein as an interaction sequence.

One or more of the created frames may be compressed as a video stream and delivered to the viewing application. A video stream with more than one frame can increase compression ratios because the compression algorithms can take advantage of the redundancy that exists not only in an intra-frame but in the inter-frame and temporal motion-compensation information of the many frames.

Following the user's interaction to select one or more views, a request is initiated to Load Balancer 90 to identify the Storage and Processing servers 102 with which to interact. The Load Balancer server determines which Storage and Processing server 102 from the available cluster is capable of servicing the user's request. The criterion for selecting which server is determined but not limited to by the size of the volume data, the capability of the server to render the volume data, current load of the server, and the location of the data. Once a server 102 is selected, the Load Balancer response to the web application and the web application creates a viewing application with the appropriate creation parameter that links the viewing application to the Storage and Processing servers. The viewing application may be a web application in the form of an Active-X component, or a Java applet or a web browser scriptable language such as JavaScript, Flash or Silverlight. The web application may display the viewing application either as one or more new web page with dynamic window size, or on full screen mode, or an embedded viewer on an existing or new web page, or launched as a stand-alone viewer. The full screen mode displays visualization on the entire screen or desktop or on multiple monitors.

Once the application is initiated, user 22 makes a request to the Storage and Processing server 102 to obtain desired volume data information. The volume data information may contain but not limited to aspect ratio of voxel, voxel spacing, dimension and bit depth. This allows the application to prepare the appropriate initial presentation of the volume data to a user. The Storage and Processing server loads the data from its storage medium. The loading progress of the volume data may be displayed to the user by having the volume visualization web server send video streams and by having the application display the stream. The video stream may be a collection of frames generated by the Storage and Processing server and may be compressed either through known lossless or lossy compression methods, depending on user preferences for (i) quality of visualization of processed images, and (ii) interaction frame rates. Depending on these two parameters and the network bandwidth and latency (discussed further below), the Storage and Processing server may choose the appropriate compression type. The compression algorithm can either be executed on central processing unit (CPU) or graphics processing unit (GPU) at server 102. Use of GPU and machine-learning techniques can be applied to enhance compression ratio and performance.

Figure 2:
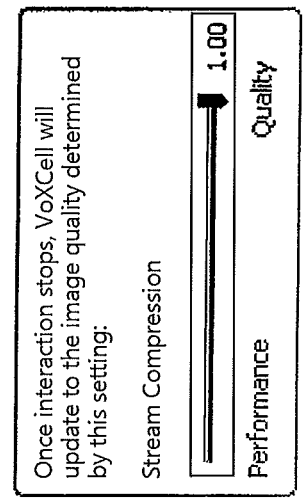
FIG. 2 shows the requests that may be made by the client computer for transmission of frames of views of the volume visualization dataset at different combinations of performance (transmission rate) and image quality.
Figure 2:
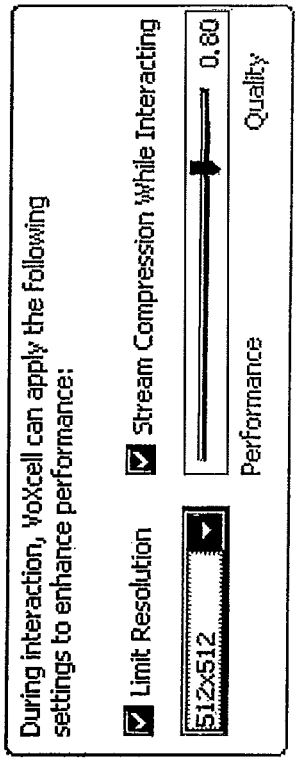

The compression parameters may be adapted but not limited to the image quality requirements of the user, and network bandwidth size. Image quality parameters may be set as an option on the application by the user to adapt to different image quality or performance during interaction, and for when the interaction has stopped. A lower image quality parameter for the frames may be transmitted over the Internet from the server 102 to the user device 22 at a faster rate than a higher image quality parameter for the frames. As shown in FIG. 2, a request 110 may be made by the user device 22 to limit frame resolution, for example to 512×512 pixels and to stream the transmission of compressed frames while user interaction occurs. The balance of frame resolution may be set by the slide which ranges from high performance (transmission rate) and low image quality at the left, to low performance (transmission rate) and high image quality at the right, or any combination in between. FIG. 2 also shows that user device 22 may also transmit a request 120 to update the image quality, for example, when the user interaction stops, to a different combination of performance (transmission rate) and image quality. These options allow one to use a lower quality image to facilitate delivery of high frame rates and once interaction is stopped, an image quality with highest fidelity may be restored. Once the application 30 receives the stream, it may decompress the stream to retrieve individual frames contained within the video stream, and displays each frame successively at the user device with the appropriate timing.

The server may transmit the higher image quality parameter frames to the client device while the client device is displaying the lower image quality parameter frames, and the client device may display the higher image quality parameter frames prior to or after completing display of the lower image quality parameter frames.

When the volume data is fully loaded or while the volume is being loaded, user 22 is allowed to interact with the partially and progressively loaded volume. Such interaction begins by the user manipulating the application 30 user interface to perform function such as but not limited to orientation such as zoom, rotate, pan, cross reference, threshold adjustment, window/level adjustment, transfer function manipulation, drag and drop to control the layout of multiple volumes, fusion to manipulate the combining of two or many volumes, segmentation to remove parts of the volume or simplify the visualization of the volume, supervision for machine learning input, and the like.

A user interaction sequence may be described as simple keyboard or mouse action, or as a complex graphical state such as ones presented by OpenGL standard, or combined with other peripheral information pertaining to generating an advanced visualization of the volume dataset. An interaction sequence is encapsulated as but not limited to an XML document. User interaction sequences may be communicated to Storage and Processing server 102 using a standard interprocess communication (IPC) technology by invoking its appropriate procedure. In an IPC request, a server 102 procedure name and parameters is encapsulated using but not limited to an XML document. The procedure may be executed but not limited to using either through a secure remote procedure call (RPC), or through an encrypted XML on hypertext transfer protocol (HTTP), or through a hypertext transfer protocol secure (HTTPS). The information returned to the user of a procedure may also be in the form of an XML document. The IPC communication is secured by encrypting the channel; for example HTTPS protocol provide default SSL/TSL encryption while other protocols may be encrypted using a public key and private key combination. The user may exit the application using the application's close function, for example, by selecting a logout command on the web page on which the user or program logged in initially.

Figure 4:
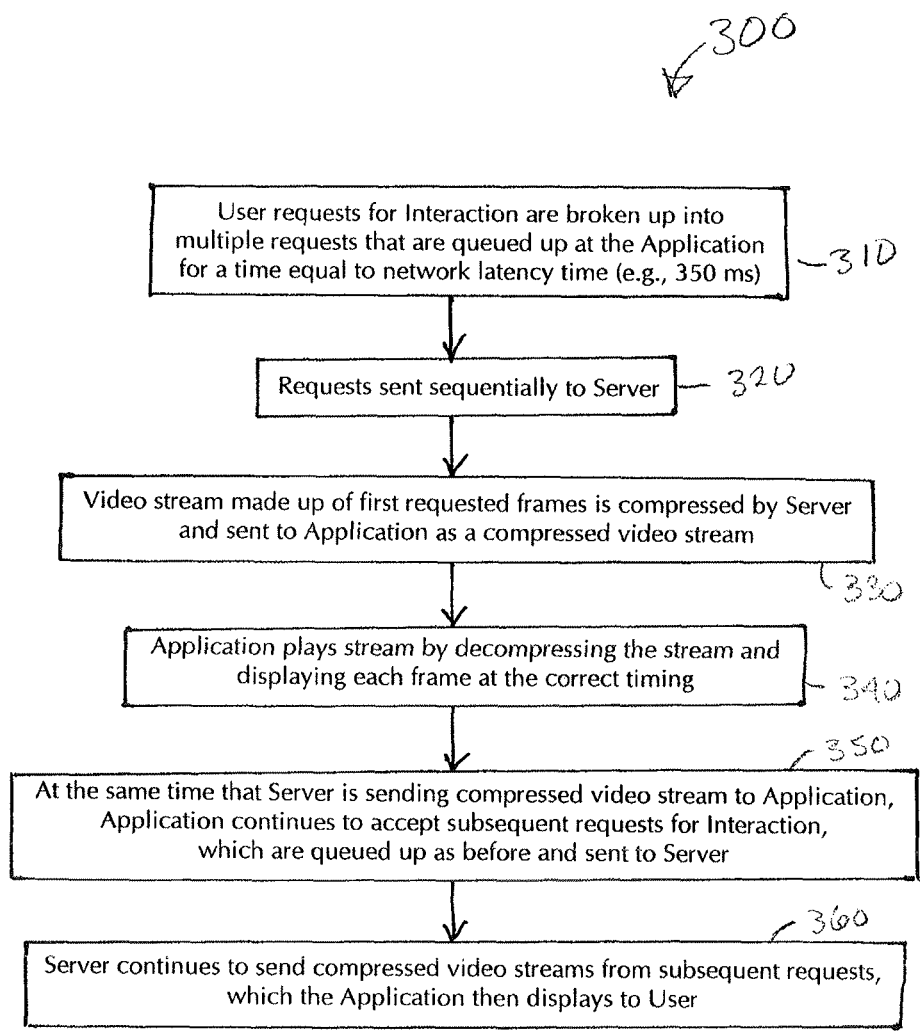
FIG. 4 is a flow diagram showing one embodiment of the method of reducing delays in displaying view frames transmitted from a central server and data storage due to network latency.
Figure 5:
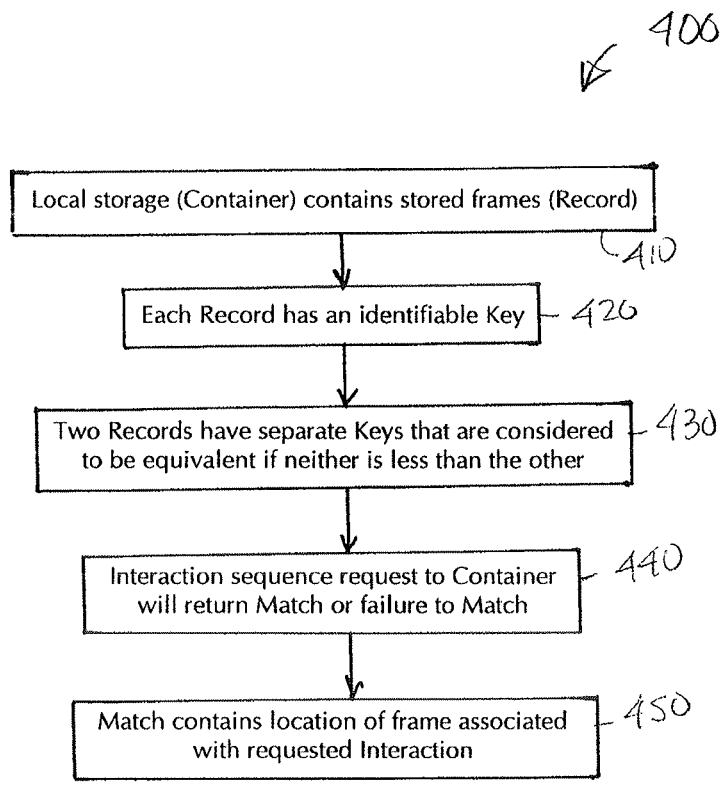
FIG. 5 is a flow diagram showing one embodiment of the method of rapidly determining if requested view frames are available on the user's local storage medium.

To overcome the network latency between the application 30 and server 102, the user interactions are queued up to the network latency time (usually less than 300-350 milliseconds) and then the collection of user interactions are sent to the Storage and Processing server. As shown in FIG. 4, the method of reducing delays in displaying view frames transmitted from a central server 300 includes step 310, where a user's requests for interaction are broken up into multiple requests that are queued up at Application 30 for a time equal to network latency time (e.g., 350 ms). Next, in step 320, the requests are sent sequentially to server 102. The Storage and Processing server generates images as frames for each user interaction and generates a video stream from the collection of frames. In step 330, the video stream made up of first requested frames may be compressed by server 102 either through lossless or lossy compression scheme and sent to application 30, for example, as a compressed video stream. The application may then play this video stream by decompressing the stream and displaying each frame at the correct timing (step 340). During the time the volume visualization web server is rendering and sending the video stream back to the application, the user interaction sequences may be continuously accepted by the application, and the interactions may be queued up according to the network latency time as described previously and sent to the server (step 350). The process of gathering interaction sequence, sending those sequences to the web server and playing the video stream of the previous interaction sequences may be repeated until the user 22 stops interacting. The server continues to send compressed video streams from subsequent requests, which the application then displays to the user (step 360). By overlaying the collection of user interactions sequences at the application end, and with the processing time for generating the video streams by server 102, the network latency and rendering time can be virtually hidden. For example, assume that the network latency time is 300 ms, and during that time, user interactions sequences are being collected. When the sequences are submitted at 300 ms time, the video stream of the previous sequence has now become available. Hence, after an initial lag of 300 ms, the interaction may be made smooth because the application is continuously collecting new user interactions sequence and playing back video streams of the previous sequence. The playback of the video stream needs may be done at the correct timing to make the video stream of images play seamlessly.

A user interaction and/or interaction sequences along with the corresponding frame or video stream that has been obtained from the Storage and Processing servers may be tracked and kept in available computer-readable storage medium 24 on the user's computer by the application. The frame may be kept as it is or in a compressed form; lossless compression may be preferred to retain the original image quality but near lossless or lossy compression algorithms may also be acceptable. This enables the application to reuse the frame or video stream when a user performs the same interaction or interaction sequences without having to request it from the volume visualization web server, thereby eliminating network traffic and increasing display performance.

Figure 3:
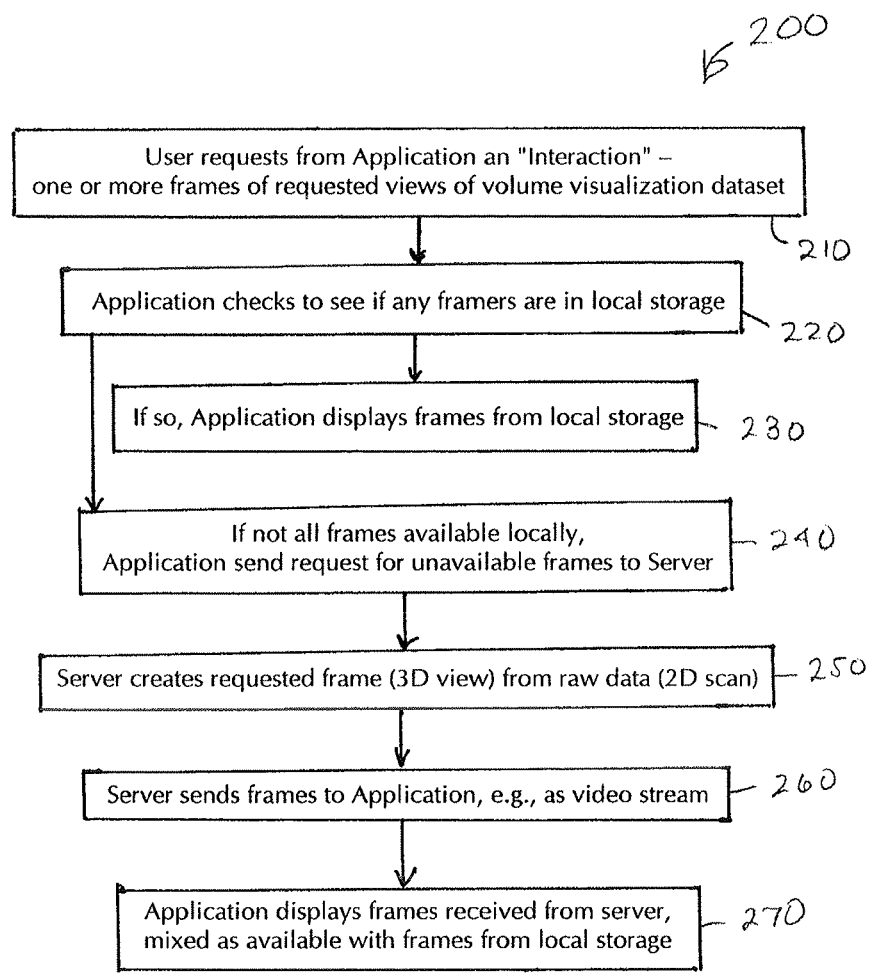
FIG. 3 is a flow diagram showing one embodiment of the method of combining local- and server-stored images of frames of the volume visualization dataset.

The present invention provides a method of combining local- and server-stored images of frames of the volume visualization dataset, as depicted in FIG. 3. The method 200 provides that a user 22 may request from application 30 at the client device an interaction, i.e., one or more frames of three-dimensional virtual views of volume visualization dataset (step 210). The application checks to see if any requested frames are stored on local storage medium 24 (step 220). If so, the application displays the frames from the local storage medium. If all requested frames not available locally, the application send request for unavailable frames to server 102 (step 240). The server then creates the requested frame, i.e., a 3D view, from raw data, i.e., the 2D scans stored in the volume visualization dataset in the central storage medium (step 250). The server then transmits the created frame(s) to the application the client device, e.g., as a video stream (step 260). The application then displays frames received from the server, optionally mixed with frames available from local storage (step 270).

Identification of such repeated user interactions and the corresponding stored frames or video stream should be done as rapidly as the sequence of frames is to be displayed to the user. For example, the entire lookup and rendering have to be done at least within one-eighth of a second to deliver an acceptable 8 frame per second (FPS) interactivity and display. One method 400 for rapid retrieval is to use a sorted associative container in local storage medium 24, as depicted in the flow diagram of FIG. 5. When a 3D view frame is transmitted from the server 102 to the user 22, a copy is stored in the user's local storage medium 24. The local storage medium may include a container that has stored frames in a record created by a previous request by the user of a 3D view (step 410). In a sorted associative container, a record is obtained by providing to the container an identifiable key (step 420). Two records within such a container have two separate keys which are considered to be equivalent if neither one is less than the other (step 430). Elements of a user interaction XML document can be compared with another to determine whether the values of the elements in either one are less than the other. So, a unique identifiable key may be made for user interaction XML document. Presenting a user interaction sequence to the container will result in the container returning either a match or a failure to match (step 440).

A match may contain the information of the location of the frame associated with that particular user interaction, for example a memory address of the frame or a file name of the frame (step 450). Where a web application is written in scripting language such as JavaScript, the recollection of rendered frames may be done by utilizing the web browser's caching mechanism. A browser may identify such image through its uniform resource locator (URL) address. By providing the browser with the same URL for a user interaction that has been executed before, the network communication to a server is eliminated. Thus when an interaction sequence is created in response to a user's request, the interaction sequence may be encapsulated as an XML document, and this XML document may be used to query the associative container. If a match is found, a round trip to server is avoided entirely and the frame stored is used instead.

By keeping track of user interaction sequences and its corresponding rendered frames, bandwidth usage and server resources may be sufficiently enhanced so that the interactive performance of applications in low bandwidth conditions is possible. For example, a Radiologist user may move from one Sagittal cross section to another (commonly known as "Stacking"). When the user returns to the previous cross section, the rendered frame is immediately retrieved without making a round trip to the server. Similarly, if a user does a 360 degrees rotation at 10 degrees interval (commonly known as "360-view"), then after 36 requests to the server, all the frames needed to perform subsequent 360 rotation have already been obtained. This enables the user to continue to rotate in either direction of the 360 degrees by using only the frames stored on local storage medium 24, without application 30 needing to request the frames from server 102. Also, when the user interface is set to a specific tool, for example, Stacking or 360-view, the application can predict all combinations of user interaction sequence. A user may elect to automate the pre-fetching of interaction sequences when prediction by application is possible. After a short wait, all the frames are available for interaction for the given set of interaction sequences. In summary, by keeping track of user interactions parameters and the corresponding locally stored frames, and by having a rapid way to identify the current user interaction with previous interaction parameters, as well as automating pre-fetching of interaction sequences, the present invention is able to achieve interactivity over low bandwidth and high latency networks.

Keeping track of user interaction sequences and its corresponding rendered frames also enables the display of 4D or higher dimensional dataset at interactive frame rates over low bandwidth. An element of a user interaction sequence is reserved to indicate which scan is currently being rendered. Suppose a cardiac scan of a patient contains a time series of 16 scans taken at various interval of the heart beat cycle. So, after iterating through the 16 scans and rendering each view and with other elements of the user interaction sequence fixed, the playback of the 16 scans results in a real-time animated sequence of the heart. This is because none of the 16 views require a round trip to the server. This makes it possible to display interactively 4D or higher dimensional data over low bandwidth.

The Storage and Processing servers may render a volume visualization dataset as described in U.S. patent application Ser. No. 11/672,581, publication no. US 2008/195843, for Method and System for Processing a Volume Visualization Dataset, filed on Feb. 8, 2007, the disclosure of which is hereby incorporated by reference. Machine learning algorithms may be applied to the processing of volume visualization dataset, for example, during segmentation of a volume to provide semi-automatic segmentation through unsupervised and supervised learning techniques. Genetic algorithms, self organizing maps and neural networks may be utilized to process the volume visualization.

The Storage and Processing Layer 100 may have: 1) server hardware equipped with one or multiple operating systems using zero or multiple virtual machines, 2) one or many computer program(s) responsible for accepting and responding to viewing application in accordance to HTTP and/or HTTPS, 3) one or many computer program responsible for accepting and responding to viewing application in accordance to User Datagram Protocol, 4) one or many computer program(s) responsible and responding to a network monitoring system, have one or many central processing unit (CPU), 5) one or many co-processors, which may include field programmable gate arrays (FPGAs), vector processors like the graphics processing unit (GPU), cell processors, or co-processors embedded in the same physical chip as the CPU, and/or 6 ) storage devices such as random access memory, flash memory, solid state drive or hard disk, or any one or more of the additional above-mentioned computer readable storage mediums.

The entire cluster of servers 102 behind the firewall 76 may be networked with high speed link such as GigE, 10 GigE or Infiniband switch through but not limited to standard Category 5 cable or fiber optic cables. This enables the servers to transmit or exchange data between these servers at a high speed. The server clustered may be connected 55 to the Internet using an external service provider such as AT & T network carrier by connecting the external link to the switch. The server clusters may be networked privately within carrier neutral data centers so each servers can communicate on different sites rapidly. A network monitoring system is utilized to identify the network for problems caused by overloaded and/or crashed servers, network connections or other devices on the network.

For compliance with applicable regulations and for protecting the Storage and Processing servers clusters, the Security, Load Balancer and Storage and Processing Layers in each of serving sites 70, 70' may be installed at a SAS70 Type II Compliant data center pursuant to periodic statements issued by the Auditing Standards Board of the American Institute of Certified Public Accountants (AICPA). In such a data center, logs of user entering or leaving are recorded, the facility is physically protected through but not limited to fingerprint, handprint or other biometric base identity entry system, the racks or cages are locked and monitored via cameras, and a hardware firewall and intrusion detection are installed and monitored to fend off cyber attacks. Only ports that enable web methods are opened on the firewall. Examples of standard ports are 80 for HTTP or 443 for HTTPS. A private UDP port may also be opened to provide a better video streaming experience to the viewing application. An intrusion detection and prevention system 74 may be used to detect several types of malicious behaviors that can compromise the security and trust of a clustered system. This includes network attacks against vulnerable services, data driven attacks on applications, host based attacks such as privilege escalation, unauthorized logins and access to sensitive files, and malware (viruses, trojan horses, and worms). The communication between the web application and the Storage and Processing servers may be encrypted. A VPN access through a function of the firewall device may be enabled for remote monitoring and updating of cluster of servers behind the firewall. From within a VPN session, authorized remote desktop applications may be enabled to gain remote access to the servers.

The present invention may be embodied as a system, method or computer program product. The present invention may take the form of an entirely hardware embodiment, an entirely software embodiment (including firmware, resident software, micro-code, etc.) or an embodiment combining software and hardware aspects that may all generally be referred to herein as a "circuit," "module" or "system." The present invention may take the form of a computer program product embodied in one or more computer readable medium(s) having computer readable program code embodied thereon. Program code embodied on a computer readable medium may be transmitted using any appropriate medium, including but not limited to wireless, wireline, optical fiber cable, radio frequency (RF) or the like, or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described herein with reference to diagrams of function blocks or modules in the drawings showing methods, apparatus (systems) and computer program products according to embodiments of the invention. It will be understood that each block and combinations of blocks in the drawings may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the function blocks or modules in the drawings.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the function blocks or modules in the drawings.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the function blocks or modules in the drawings.

The function blocks or modules in the drawings illustrate the architecture, functionality, and operation of possible implementations of systems, methods and computer program products according to various embodiments of the present invention. In this regard, each block in the drawing may represent a module, segment, or portion of code, which comprises one or more executable instructions for implementing the specified logical function(s). It should also be noted that, in some alternative implementations, the functions noted in the block may occur out of the order noted in the figures. For example, the function of two blocks shown in succession may, in fact, be executed substantially concurrently, or the blocks may sometimes be executed in the reverse order, depending upon the functionality involved. It will also be noted that each block and combinations of blocks in the drawing may be implemented by special purpose hardware-based systems that perform the specified functions or acts, or combinations of special purpose hardware and computer instructions. Also, although communication between function blocks or modules may be indicated in one direction on the drawing, such communication may also be in both directions.

The present invention therefore provides a processing and access mechanism that overcomes low bandwidth and high latency limitations that are inherent properties of the standard Internet and permits bandwidth usage to be optimized, particularly for interactive web application for visualizing large medical scans on any Internet connection.

The present invention also overcomes the problems of maintaining medical records for long periods of time under security and privacy by providing a method and system of a common and centralized infrastructure, for receiving, storing, processing and viewing large medical scans via a web portal where economic of scale can be applied generously.

The present invention further provides fast access to imaging studies and immediate 3D manipulation of the dataset over a standard, low bandwidth, Internet connection. The present invention permits one to carry out one or more of the following specific aims to empower radiologists, clinicians, surgeons and patients to access medical scans: A HIPAA compliant and secure web portal for fast access by physicians and patients enables sharing of medical scans between participating health care institutions systems using DICOM and HL7 standards. Also, patients are able to upload their scan from a CD or by providing their consent to obtain the scans from non-participating institutions on the patient's behalf. This enables hospitals to interface with any physicians or specialist from anywhere, allows the physicians to communicate among themselves and with patients effectively, and enables patients, especially in rural areas, have access to any physicians anywhere to provide proper diagnosis or second opinions. The portal is based on centralized and high performing vector processor based clustered servers for generating easy to comprehend 2D, 3D or 4D intelligent visualization of large scans and transmitting those views to end users.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A system for viewing at a client device at a remote location a series of three-dimensional virtual views over the Internet of a volume visualization dataset contained on at least one centralized database comprising:
   at least one transmitter for accepting volume visualization dataset from remote location and transmitting it securely to the centralized database;
   at least one central data storage medium containing the volume visualization dataset;
   a plurality of servers in communication with the at least one centralized database and capable of processing the volume visualization dataset to create virtual views based on client request;
   a resource manager device for load balancing the plurality of servers;
   a security device controlling the plurality of communications between a client device, and the server; including resource manager and central storage medium;
   at least one physically secured site for housing the centralized database, plurality of servers, at least a resource manager, and at least a security device;
   a web application adapted to satisfy a user's request for the three-dimensional virtual views by: a) accepting at a remote location at least one user request for a series of virtual views of the volume visualization dataset, the series of views comprising a plurality of separate view frames, the remote location having a local data storage medium for storing frames of views of the volume visualization dataset, b) determining if any frame of the requested views of the volume visualization dataset is stored on the local data storage medium, c) transmitting from the remote location to at least one of the servers a request for any frame of the requested views not stored on the local data storage medium, d) at at least one of the servers, creating the requested frames of the requested views from the volume visualization dataset in the central storage medium, e) transmitting the created frames of the requested views from at least one of the servers to the client device, f) receiving the requested views from the at least one server, and displaying to the user at the remote location the requested series of three-dimensional virtual views of the volume visualization dataset by sequentially displaying frames transmitted from at least one of the servers along with any frames of the requested series of views stored on the local data storage medium.

2. The system of claim 1 wherein a secured site is a SAS70 Type II Compliant or equivalent audited or tested data center.

3. The system of claim 1 wherein multiple secured sites located on disparate physical location are connected via an intranet.

4. The system of claim 1 wherein the web application is adapted to select a secured site by using a domain name address on a web browser.

5. The system of claim 4 wherein the web application is adapted to select a secured site IP address of a resource manager by Domain Name System.

6. The system of claim 1 wherein the web application is categorized as a medical device for diagnostic imaging viewing purpose.

7. The system of claim 1 wherein the web application is adapted to be authenticated using an authorized user credentials prior to transmitting the request to at least one of the servers.

8. The system of claim 7 wherein an authenticated web application lists the volume visualization datasets that are viewable by the authorized user.

9. The system of claim 8 wherein the web application initiates a virtual viewing by selecting a volume visualization dataset.

10. The system of claim 7 wherein the web application is adapted to communicate with the resource manager device.

11. The system of claim 10 wherein the web application is allocated with at least one server by the resource manager device.

12. The system of claim 11 wherein the web application is adapted to commence interaction with the at least one server to satisfy user requests.

13. The system of claim 1 wherein the web application is an Active-X component, a Java applet or JavaScript, Flash or Silverlight or other web browser scriptable language.

14. The system of claim 1 further including an encrypted communication connection over which the request and the resulting virtual view are transmitted.

15. The system of claim 14 wherein the encrypted communication connection employs SSL/TLS and further including secure communication ports that communicate only with SSL/TLS turned on.

16. The system of claim 1 wherein the request for a virtual view of the volume visualization dataset employs an XML document or web server on Hypertext Transfer Protocol Secure (HTTPS).

17. The system of claim 1 wherein, during the displaying of the requested series of three-dimensional virtual views of the volume visualization dataset at the remote location, the web application causes frames stored on the local data storage medium to be displayed along with frames transmitted from the server.

18. The system of claim 1 wherein the volume visualization dataset comprises a plurality of cross-sectional images taken at spaced intervals through an object.

19. The system of claim 1 wherein the web application determines storage of any frame of the requested views of the volume visualization dataset on the local data storage medium is by:
   creating a unique identifiable key of a request by the remote location of a three-dimensional virtual view of the volume visualization dataset;
   storing on the local data storage medium the unique identifiable key of a prior request by the remote location of a three-dimensional virtual view;
   comparing the unique identifiable key of a current request by the remote location of a three-dimensional virtual view with a stored unique identifiable key of a prior request by the remote location of a three-dimensional virtual view;
   determining if values of the current and prior unique identifiable keys are equivalent;
   if the values are equivalent, displaying from the local data storage medium a stored frame of the prior request of the three-dimensional virtual view; and
   if the values are not equivalent, displaying a frame transmitted from the server of the current request by the remote location of a three-dimensional virtual view.

20. The system of claim 19 wherein the web application associates the unique identifiable key of a prior request by the client device of a three-dimensional virtual view with a stored frame of the prior request of the three-dimensional virtual view.

21. The system of claim 19 wherein, if the values are equivalent, the web application determines location of the stored frame of the prior request of the three-dimensional virtual view on the local data storage medium, and uses such location to display the stored frame.

22. A system for viewing at a client device at a remote location a series of three-dimensional virtual views over the Internet of a volume visualization dataset contained on at least one centralized database comprising:
    at least one transmitter for accepting the volume visualization dataset from the remote location and transmitting it securely to the centralized database;
    at least one central data storage medium containing the volume visualization dataset;
    a plurality of servers in communication with the at least one centralized database and capable of processing the volume visualization dataset to create virtual views based on client request;
    a resource manager device for load balancing the plurality of servers;
    a security device controlling the plurality of communications between a client device, and the server; including resource manager and central storage medium;
    at least one physically secured site for housing the centralized database, plurality of servers, at least a resource manager, and at least a security device;
    a web application adapted to satisfy a user's request by: a) accepting at the server a user request from the remote location for a plurality of three-dimensional virtual views of at least a portion of the volume visualization dataset, the plurality of views comprising a plurality of separate view frames, the request including a request for a lower image quality parameter for the frames, at a lower frame resolution, and a request for a higher image quality parameter for the frames, at a higher frame resolution, b) at the server, creating the requested frames from the volume visualization dataset at the lower image quality parameter, and transmitting the lower image quality parameter frames to the remote location, c) displaying at least a portion of the requested lower image quality parameter frames at the remote location, d) at the server, creating the requested higher image quality parameter frames from the volume visualization dataset, and transmitting the higher image quality parameter frames to the remote location, e) displaying the requested higher image quality parameter frames at the remote location, and f) after the lower image quality parameter frames is transmitted to the remote location, transmitting the higher image quality parameter frames from the server to the remote location while the remote location is displaying the lower image quality parameter frames.

23. The system of claim 22 wherein the web application causes the remote location to display the higher image quality parameter frames prior to completing display of the lower image quality parameter frames.

24. The system of claim 22 wherein the web application causes the remote location to display the higher image quality parameter frames after completing display of the lower image quality parameter frames.

25. The system of claim 22 wherein the web application causes the server to transmit the frames to the remote location as a compressed video stream.

26. The system of claim 22 wherein the web application causes the server to transmit the frames to the remote location as one or more single frames.

27. A system for viewing at a client device at a remote location a series of three-dimensional virtual views over the Internet of a volume visualization dataset contained on at least one centralized database comprising:
    at least one transmitter for accepting volume the visualization dataset from the remote location and transmitting it securely to the centralized database;
    at least one central data storage medium containing the volume visualization dataset;
    a plurality of servers in communication with the at least one centralized database and capable of processing the volume visualization dataset to create virtual views based on client request;
    a resource manager device for load balancing the plurality of servers;
    a security device controlling the plurality of communications between a client device, and the server; including resource manager and central storage medium;
    at least one physically secured site for housing the centralized database, plurality of servers, at least a resource manager, and at least a security device;
    a web application adapted to satisfy a user's request by: a) accepting at a remote location a series of three-dimensional virtual views of at least a portion of the volume visualization dataset, the series of views comprising a plurality of separate view frames, b) separating at the remote location the requested series of three-dimensional virtual views into different groups of frames, c) sending from the remote location to the server a request for a first group of frames, while delaying sending to the server a request for a second group of frames, d) at the server, creating the requested first group of frames from the volume visualization dataset, and transmitting the first group of frames to the remote location, e) displaying the requested first group of frames at the remote location while simultaneously sending from the remote location to the server a request for a second group of frames, f) at the server, creating the requested second group of frames from the volume visualization dataset, and transmitting the second group of frames to the remote location while the remote location is displaying the first group of frames, and g) displaying the requested second group of frames at the remote location immediately following the first group of frames, to maintain proper sequential display of the requested series of three-dimensional virtual views.

28. The system of claim 27 wherein the web application is further adapted to satisfy a user's request by sending from the remote location to the server a request for a subsequent group of frames while a previous group of frames is being displayed, creating at the server the requested second group of frames from the volume visualization dataset, transmitting the second group of frames to the remote location while the remote location is displaying the previous group of frames; and displaying the requested subsequent group of frames at the remote location immediately following the previous group of frames to maintain proper sequential display.

29. The system of claim 27 wherein the remote location and server are connected by a network having a latency time, and wherein the web application is further adapted to satisfy a user's request by the requested groups of frames are delayed in sending from the remote location to the server in accordance with the latency time.

30. The system of claim 27 wherein the web application is further adapted to satisfy a user's request by transmitting the groups of frames from the server to the remote location as a compressed video stream.

31. The system of claim 27 wherein the web application is further adapted to satisfy a user's request by including with the request for a first group of frames a request for a lower image quality parameter for the frames, and wherein after transmitting the first group of frames to the remote location at the requested lower image quality parameter, the server transmits frames to the remote location at a higher image quality parameter.

* * * * *